(12) United States Patent
Kumar et al.

(10) Patent No.: US 6,641,395 B2
(45) Date of Patent: Nov. 4, 2003

(54) ENDOSSEOUS IMPLANT DRILL

(75) Inventors: Ajay Kumar, Palmdale, CA (US); Steven M. Hurson, Yorba Linda, CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/920,351

(22) Filed: Aug. 1, 2001

(65) Prior Publication Data

US 2002/0031745 A1 Mar. 14, 2002

Related U.S. Application Data

(60) Provisional application No. 60/222,501, filed on Aug. 2, 2000.

(51) Int. Cl.$^7$ ................................................. A61C 3/02
(52) U.S. Cl. ........................................................... 433/165
(58) Field of Search ................................. 433/165, 166, 433/80, 102, 72, 82; 408/211

(56) References Cited

U.S. PATENT DOCUMENTS

| | | |
|---|---|---|
| 1,200,921 A | 10/1916 | Chester |
| 3,971,135 A | 7/1976 | Leu |
| 4,352,610 A | 10/1982 | Yankovoy et al. |
| 4,560,308 A | 12/1985 | Deller |
| 4,681,541 A | 7/1987 | Snaper |
| 4,787,848 A | 11/1988 | Ross |
| 4,820,156 A | 4/1989 | Ross |
| 4,859,493 A | 8/1989 | Lemelson |
| 4,943,236 A | 7/1990 | Linkow et al. |
| 4,960,643 A | 10/1990 | Lemelson |
| 5,078,605 A | 1/1992 | Sutter et al. |
| 5,098,737 A | 3/1992 | Collins et al. |
| 5,261,818 A | 11/1993 | Shaw |
| 5,299,937 A | 4/1994 | Gow |
| 5,538,423 A | 7/1996 | Coss et al. |
| 5,569,035 A | 10/1996 | Balfour et al. ............... 433/165 |
| 5,571,106 A | 11/1996 | Coufal et al. .................. 606/80 |
| 5,575,650 A | 11/1996 | Niznick et al. ............. 433/165 |
| 5,653,812 A | 8/1997 | Petrmichl et al. ............ 118/723 |
| 5,741,267 A | 4/1998 | Jorneus et al. ............... 606/102 |
| 5,747,120 A | 5/1998 | McLean, II et al. ........ 427/596 |
| 5,785,522 A | 7/1998 | Bergstrom et al. ............ 433/72 |
| 5,839,897 A | 11/1998 | Bordes ....................... 433/165 |
| 5,868,572 A | 2/1999 | Lazzara et al. ............. 433/165 |
| 5,947,659 A | 9/1999 | Mays ......................... 408/211 |
| 5,997,298 A | 12/1999 | Nowak ....................... 433/165 |
| 6,036,410 A | * 3/2000 | Shun'ko ..................... 408/230 |
| 6,319,610 B1 | * 11/2001 | Zimmer ..................... 428/408 |

FOREIGN PATENT DOCUMENTS

| | | |
|---|---|---|
| SU | 1659037 A1 | 5/1989 |
| WO | WO 00/27301 | 11/1999 |

OTHER PUBLICATIONS

U.S. patent application Ser. No. 09/439,247, Kumar, filed Nov. 12, 1999.

U.S. patent application Ser. No. 09/853,256, filed May 11, 2001, Kumar.

Synthetic Diamond: Emerging CVD Science And Technology, Edited by Karl E. Spear and John P. Dismukes, 1994, pp. 91–97, 110–112, 120–121, 134–135.

* cited by examiner

*Primary Examiner*—Kevin Shaver
*Assistant Examiner*—Melba Bumgarner
(74) *Attorney, Agent, or Firm*—Knobbe, Martens, Olson & Bear, LLP

(57) ABSTRACT

The invention provides a dental drill comprising a plurality of blades each distally terminating in an end cutting edge having a positive rake angle. Advantageously, this allows for efficient, accurate and safe formation of an endosseous implant-receiving osteotomy in a patient's jawbone. Desirably, any patient trauma or discomfort during the procedure is substantially eliminated or reduced and a precision-sized osteotomy for receiving an implant of a predetermined size is created.

55 Claims, 8 Drawing Sheets

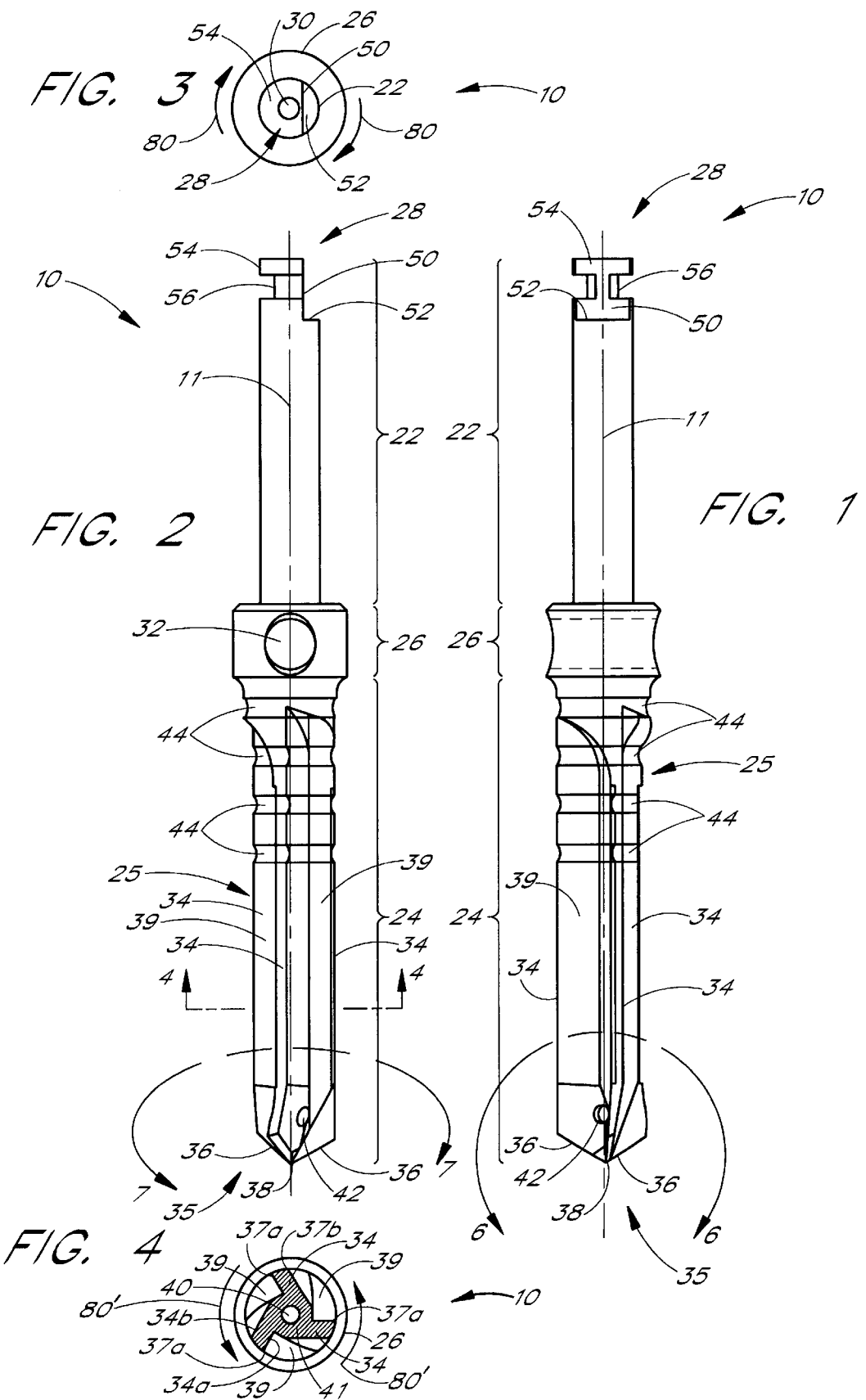

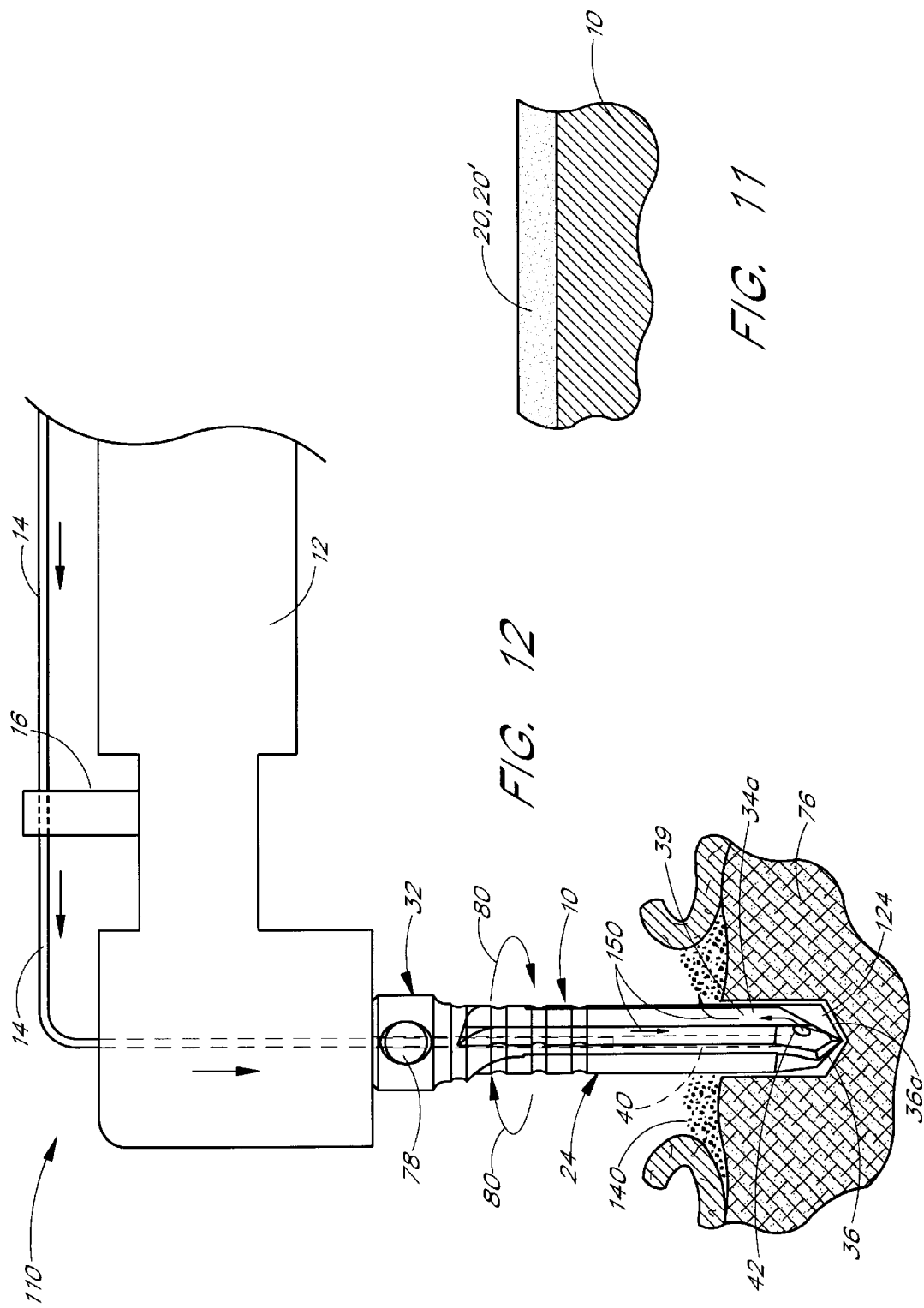

ENDOSSEOUS IMPLANT DRILL

RELATED APPLICATIONS

This application claims the benefit of U.S. Provisional Application No. 60/222,501, filed Aug. 2, 2000, the entire disclosure of which is hereby incorporated by reference herein.

BACKGROUND OF THE INVENTION

1. Field of the Invention

The invention relates to dental surgical instruments for use in the field of oral surgery, and, more particularly, to dental drill bits for use in the field of dental implantology for preparing surgical sites for placement of endosseous dental implants.

2. Description of the Related Art

Dental implants are surgically implanted in a patient's jawbone to provide securement anchors for prosthetic devices such as artificial teeth, crowns, bridges, dentures and the like. Dental implants allow people who lose their teeth to be able to comfortably smile, speak, and chew.

An oral surgeon installs a dental implant by first making an incision in the patient's gum or gingiva. Next, a hole or osteotomy is formed in the jawbone of the patient. This may involve widening of a pre-existing cavity or the formation of a fresh one. The implant is then inserted and/or threaded into the osteotomy. More than one osteotomy may be prepared to support a plurality of implants. Once the implant is properly secured in the osteotomy a healing screw is threaded tightly over the implant to seal it from bacterial infection and the gums are sutured over the sealed implant to allow the bone and surrounding tissues to heal.

During this initial healing period bone is allowed to grow and surround and retain the implant. This process is called "osseointegration." The gum tissue is also allowed to heal over the implant and the healing screw. For implants in the mandible (lower jaw), healing typically requires about three months; for implants in the maxilla (upper jaw), the healing period is usually about six months.

After the initial healing period, the overlying gum tissues are reopened by making an incision and the healing screw is removed. A suitable healing abutment is attached to the implant and extends supragingivally through the surrounding gum tissues. A second healing period ensues in which the gum tissue is allowed to heal around the healing abutment. Typically, this second healing period lasts from four to eight weeks.

After the second healing period, the healing abutment is removed from the implant. Typically, an impression is taken of the patient's mouth to facilitate the fabrication of a precision-fitted prosthesis or dental restoration. An abutment which supports the final restoration is attached to the implant and the restoration is cemented or screwed to the abutment and/or implant to complete the placement of the prosthodontic restoration in the patient's mouth.

The initial step of forming a suitable implant-receiving osteotomy in the patient's jawbone is critical to the success of the overall dental implant procedure. The size and location of the hole and its orientation in the mouth are all important for successful osseointegration of the implant. The hole is also desirably formed concentrically about its axis and has a diameter (either constant or tapered) approximately equal to or slightly smaller than the implant to be inserted.

Typically, a skilled oral surgeon forms the osteotomy using one or more specially adapted surgical drill bits. This surgical procedure requires special care to avoid discomfort and trauma to the patient. An improper technique or poorly suited surgical instrument can cause pain and shock to the patient as the drill bit penetrates the patient's jawbone. The oral surgeon must also be careful not to drill too deeply, particularly in high-density bone, as this can cause unnecessary trauma to the bone and/or surrounding tissues, thereby complicating the osteotomy preparation process.

High-speed rotation of a drill bit during formation of an osteotomy can also generate a significant amount of friction and heat. This is especially true if the osteotomy becomes filled or clogged with bone chips and/or other debris dislodged by the rotating drill bit. Too much friction and heat can cause damaging bone "necrosis" and/or burning of the surrounding bone tissues. This unnecessarily adds to the trauma and suffering of the patient and can inhibit the desired healing of the bone and osseointegration of the implant. Rotation of the drill bit within the osteotomy being formed can also exert torque forces on both the drill bit and the surrounding bone tissues. Excessive torque forces and/or heat generation can possibly result in breakage of the drill bit within the osteotomy and, in some extreme cases, possible bone fracture. On the other hand, it is desirable to perform the osteotomy procedure quickly and efficiently in order to conserve time and minimize pain and suffering by the patient.

Many conventional surgical drill bits have cutting edges that can result in undesirable side cutting or biting of the drill bit into the surrounding walls of the osteotomy, possibly undesirably expanding the diameter of the osteotomy and/or causing vibrational precessing of the drill bit within the osteotomy as it is being formed. Many such drill bits can also have a tendency to self-advance or lodge themselves deeper into the bone being cut, much like a wood screw. In some extreme cases, this can result in undesirable penetration through the jawbone and/or surrounding soft-tissues.

Moreover, many conventional surgical drill bits have a cutting tip that tends to abrade or scrape material rather than cutting it. Disadvantageously, this can require a high torque or force to be applied to advance the drill bit. Moreover, due to the geometry of the cutting tip such drill bits are typically not very efficient and are prone to becoming clogged with bone chips and/or other debris if adequate care is not taken during use.

SUMMARY OF THE INVENTION

In accordance with one embodiment, a dental drill comprises a plurality of blades each distally terminating in an end cutting edge having a positive rake angle. Advantageously, this allows for efficient, accurate and safe formation of an endosseous implant-receiving osteotomy in a patient's jawbone. Desirably, any patient trauma or discomfort during the procedure is substantially eliminated or reduced and a precision-sized osteotomy for receiving an implant of a predetermined size is created.

In accordance with another embodiment, a drill bit is provided for preparing surgical sites for placement of endosseous dental implants. The drill bit generally comprises a mounting shank and a distal cutting head. The mounting shank has a chuck at a proximal end sized and configured to interface with a rotation providing hand-piece. The distal cutting head comprises a plurality of blades. Each blade has a positive rake angle end cutting edge converging radially from substantially an outer-most diameter of the cutting head to substantially a distal-most point of the cutting head.

In accordance with still another embodiment, a surgical drill bit is provided for forming an osteotomy in the jawbone of a patient for receiving a dental implant. The drill bit generally comprises a shank comprising a mounting portion, a working portion and having a longitudinal axis. The working portion including multiple blades each distally terminating in an end cutting edge. Each end cutting edge converges radially from substantially an outer-most diameter of the working portion to substantially a distal-most point of the working portion. Each end cutting edge has a positive rake angle. At least one of the end cutting edges has the positive rake angle only on a portion spaced from the distal-most point of the working portion and extending substantially to the outer-most diameter of the working portion.

In accordance with yet another embodiment, a dental tool bit is provided for forming an endosseous implant-receiving osteotomy in bone material. The dental tool bit generally comprises a shank having a rotary longitudinal axis. The shank generally comprises a mounting portion and a working portion. The mounting portion is adapted to interface with a dental hand-piece. The working portion has a distal terminus and an outer-most perimeter. The working portion comprises a plurality of blades extending parallel to the longitudinal axis. Each blade distally terminates in an end cutting edge. At least one of the end cutting edges has a positive rake angle. At least one of the end cutting edges has a positive rake angle along substantially its entire span extending radially from substantially the distal terminus of the working portion to substantially the outer-most perimeter of the working portion.

In accordance with one embodiment, a dental drilling system is provide for preparing an osteotomy. The drilling system generally comprises a tool bit and a dental hand-piece. The tool bit has a cutting tip comprising a plurality of blades. Each blade distally terminates in an end cutting edge having a positive rake angle spanning substantially its entire length. At least one of the end cutting edges diverges from substantially a distal terminus of the cutting tip to substantially an outer-most periphery of the cutting tip. The dental hand-piece holds the tool bit and is adapted to provide rotational motion to the tool bit.

In accordance with another embodiment, a dental tool bit is provided for forming an implant-receiving osteotomy in a jawbone. The tool bit comprises a shank having a substantially central longitudinal axis and a direction of rotation. The shank generally comprises a mounting portion and a working portion. The mounting portion has a chuck at a proximal end adapted to interface with a rotary dental hand-piece. The working portion has a distal-most point and an outer-most perimeter. The working portion comprises a plurality of blades extending substantially parallel to the shank longitudinal axis. Each of the blades has a leading surface distally terminating in an end cutting edge. Each end cutting edge extends radially from substantially the distal-most point of the working portion to substantially the outer-most perimeter of the working portion. At least one of the leading surfaces is angled relative to the shank longitudinal axis such that it is tilted away from the shank direction of rotation.

In accordance with one embodiment, a method is provided of forming an osteotomy in bone material for receiving a dental implant. The method uses a drill bit having a cutting tip comprising a plurality of blades. Each blade has a positive rake angle end cutting edge converging radially from substantially an outer-most diameter of the cutting tip to substantially a distal-most point of the cutting tip. The method comprises the step of positioning the drill bit at a selected osteotomy site. The drill bit then engages the bone material. Rotational motion is provided to the drill bit to cut the bone material due to the rotational interaction between the positive rake angle end cutting edges and the bone material to form the osteotomy.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 1 is a side elevation view of a dental drill bit having features and advantages in accordance with one embodiment;

FIG. 2 is a side elevation view of the drill bit of FIG. 1 rotated 90 degrees;

FIG. 3 is a proximal end view of the drill bit of FIG. 1;

FIG. 4 is a transverse cross-section view of the drill bit of FIG. 2 taken along line 4—4;

FIG. 11 is a schematic detail view of a dental drill bit illustrating a coating formed thereon in accordance with one embodiment;

FIG. 12 is a side view of a dental drill bit illustrating its use with a dental hand-piece to form an osteotomy in accordance with one embodiment.

DETAILED DESCRIPTION OF THE PREFERRED EMBODIMENTS

Figure 5:
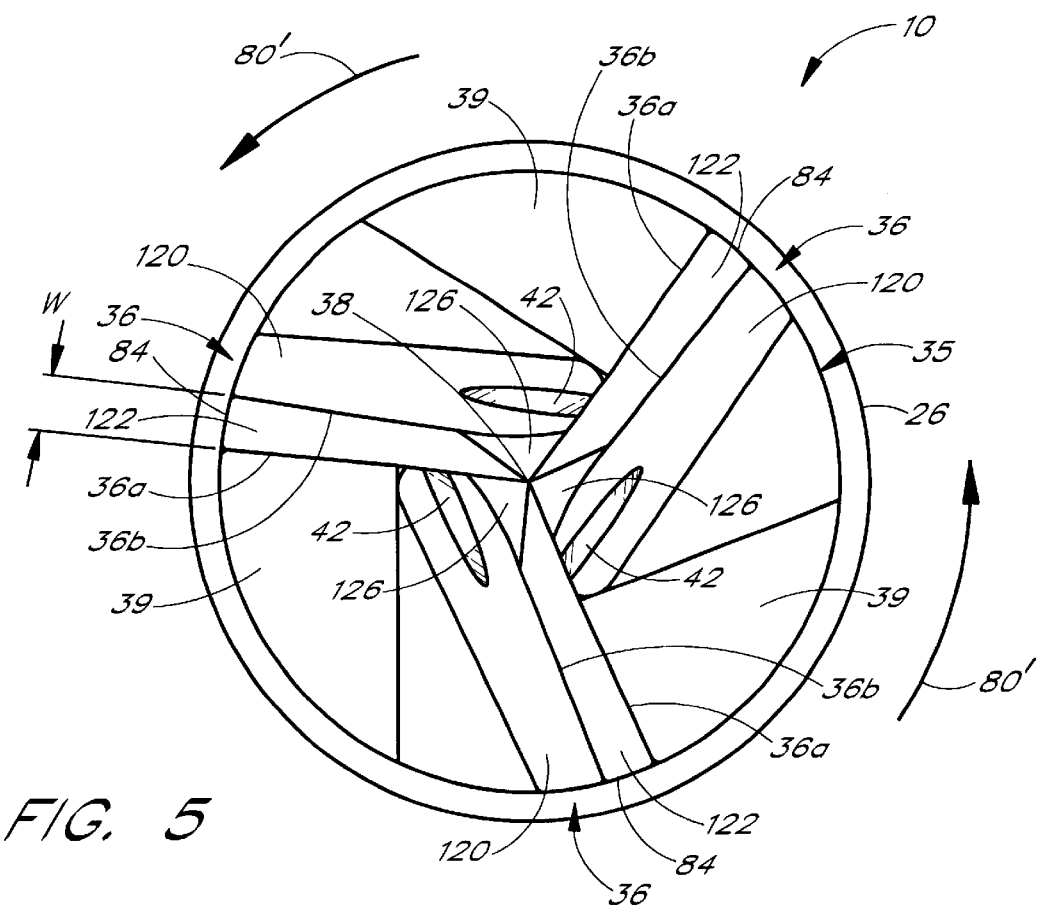
FIG. 5 is a distal end view of the drill bit of FIG. 1 illustrating a cutting tip thereof in accordance with one embodiment.

FIGS. 1–8 show several different views of a surgical dental drill bit 10 having certain features and advantages in accordance with the present invention. As will be explained in detail below, the drill or tool bit 10 is particularly adapted for forming an osteotomy or hole in the jawbone of a patient for the introduction of an endosseous implant.

In the illustrated embodiments, and with initial reference to FIGS. 1–5, the surgical tool or drill bit 10 generally comprises a shank 25 having a proximal portion 22 adapted for mounting to a dental hand-piece and a working portion 24 adapted to cut or remove bone and/or tissue material. Intermediate the working portion 24 and the proximal mounting portion 22 of the shank 25 is a collar 26. The drill bit 10 and/or the shank 25 has a generally longitudinal centerline rotary axis 11.

The dental drill bit or instrument 10 of the illustrated embodiments is adapted to rotatingly cut in a clockwise direction, as generally indicated by arrows 80. When viewed from a distal direction this clockwise rotation is generally indicated by arrows 80'. Of course, as the skilled artisan will recognize, the drill bit 10 can be efficaciously configured to rotatingly cut in a counter clockwise direction, as needed or desired.

In the illustrated embodiments, and as best seen in FIGS. 1 and 2, the proximal mounting portion 22 and the working portion 24 are formed as a single integral structure. In another embodiment, the proximal mounting portion 22 and the working portion 24 are formed separately and secured to one another at the collar 26. In other embodiments, the proximal mounting portion 22 and the working portion 24 may be efficaciously configured in a modified manner, as required or desired, giving due consideration to the goals of providing a suitably strong drill bit 10, and/or of achieving one or more of the benefits and advantages as disclosed, taught or suggested herein.

In the illustrated embodiments, and as best seen in FIGS. 1 and 2, the mounting shank 22 is generally cylindrical in shape. In other embodiments, the mounting shank 22 may be efficaciously configured in a modified manner, as required or desired, giving due consideration to the goals of providing reliable attachment to a dental hand-piece or the like, and/or of achieving one or more of the benefits and advantages as disclosed, taught or suggested herein.

In the illustrated embodiments, the mounting shank includes a proximal end or chuck 28 (see FIGS. 1–3) sized and configured to be received by a conventional dental hand-piece or drill. The chuck 28 is substantially D-Shaped in cross-section (see FIG. 3) and includes a generally I-shaped flat side 50 (see FIG. 1) which defines a step 52 and a generally semicircular disk 54 above and adjacent to a generally semi-circular groove 56. Such a chuck configuration is particularly adapted for interfacing with dental drills, hand-pieces and/or other powered surgical implements. In other embodiments, the mounting shank 22 and/or chuck 28 may be efficaciously configured in a modified manner, as required or desired, giving due consideration to the goals of connecting the drilling bit 10 to a dental drill or hand-piece, and/or of achieving one or more of the benefits and advantages as disclosed, taught or suggested herein.

In the illustrated embodiments, and as best seen in FIG. 3, the mounting shank 22 includes a generally longitudinal irrigation passage 30. The passage 30 extends from the proximal end 28 to the collar 26. The passage 30 is generally cylindrical in shape and is located substantially centrally within the mounting shank 22. The passage 30 is dimensioned and configured to accommodate insertion of an irrigation cannula, as discussed later herein, for washing away bone debris/chips (and tissue) and lubricating and cooling the drilling bit 10. In other embodiments, the irrigation passage 30 may be efficaciously dimensioned and configured in a modified manner, as required or desired, giving due consideration to the goals of providing efficient drilling performance, and/or of achieving one or more of the benefits and advantages as disclosed, taught or suggested herein.

In the illustrated embodiments, and as best seen in FIGS. 1–2, the collar member 26 is generally cylindrical in shape. In other embodiments, the collar member 26 may be efficaciously configured in a modified manner, as required or desired, giving due consideration to the goals of providing attachment or coupling between the mounting shank 22 and working portion 24, and/or of achieving one or more of the benefits and advantages as disclosed, taught or suggested herein.

In the illustrated embodiments, the collar member 26 includes a through hole 32 (see FIG. 2) which extends transversely through the collar 26. The through hole 32 is thus provided in communication with the irrigation passage 30 (see FIG. 3) of the mounting shank 22. In the illustrated embodiment, the hole 32 is sized and configured to receive a silicone plug or seal. The plug serves to hold an irrigation cannula in place and prevent undesired back-flow of cooling fluid through the irrigation passage 30, as illustrated later herein. In other embodiments, the collar 26 and/or through hole 32 may be efficaciously configured in a modified manner, as required or desired, giving due consideration to the goals of providing efficient drilling performance, and/or of achieving one or more of the benefits and advantages as disclosed, taught or suggested herein.

In the illustrated embodiments of FIGS. 1–8, the working portion 24 of the drill bit 10 includes a plurality of generally longitudinal channels 39 (see FIGS. 1–2 and 4–5) cut into the lateral surfaces or exterior of the shank 25. The channels 39 define a plurality of generally longitudinal or axial blades 34. The blades 34 terminate distally in a cutting head or tip 35 comprising end cutting blades 36 and a distal end or terminus 38.

Preferably, and as best seen in FIGS. 1 and 2, the blades or flutes 34 of are generally straight extending substantially parallel to the drill longitudinal axis 11. Advantageously, such a configuration prevents undesirable cork screwing of the drill into the material being cut as is a problem with many conventional spiral or helical drills.

In the illustrated embodiments, and as best seen in FIGS. 4 and 5, the channels 39 are generally V-shaped or generally L-shaped. In other embodiments, the channels 39 may be efficaciously configured in a modified manner, as required or desired, giving due consideration to the goals of providing efficient and/or accurate drilling performance, and/or of achieving one or more of the benefits and advantages as disclosed, taught or suggested herein.

In the illustrated embodiments, the blades 34 are arranged generally symmetrically about a central core or web 41 (see FIG. 4). In other embodiments, the blades 34 may be efficaciously arranged and/or configured in a modified manner, as required or desired, giving due consideration to the goals of providing efficient and/or accurate drilling performance, and/or of achieving one or more of the benefits and advantages as disclosed, taught or suggested herein.

Preferably, and as best seen in FIGS. 1 and 2, the blades 34 extend substantially parallel to the shank longitudinal axis 11 along substantially most of the length or the entire length of the working portion 24. In other embodiments, one or more of the blades 34 may be efficaciously arranged and/or configured in a modified manner, as required or desired, giving due consideration to the goals of providing efficient and/or accurate drilling performance, and/or of achieving one or more of the benefits and advantages as disclosed, taught or suggested herein.

Preferably, and as shown in the illustrated embodiments, the working portion 24 includes three blades 34 (see, for example, FIGS. 1 and 2). Advantageously, such a configuration provides for smooth and accurate drilling with substantially no wobbling. In another embodiment, the working portion 24 includes between three and six blades 34. In other embodiments, the working portion 24 may comprise more blades 34 with efficacy, as required or desired, giving due consideration to the goals of providing smooth and/or accurate drilling performance, and/or of achieving one or more of the benefits and advantages as disclosed, taught or suggested herein.

In the illustrated embodiments, and as best seen in FIG. 4, the working portion 24 includes three blades 34 approximately equally spaced 120° apart about the shank 25 or longitudinal axis 11. In other embodiments, the working portion 24 may comprise more blades 34 spaced apart in other angular configurations with efficacy, as required or desired, giving due consideration to the goals of providing efficient and/or accurate drilling performance, and/or of achieving one or more of the benefits and advantages as disclosed, taught or suggested herein.

In the illustrated embodiments, each blade 34 (see FIG. 4) comprises a leading blade surface 34a and a trailing blade surface 34b, a leading side edge 37a and a trailing side edge 37b. In one embodiment, one or more of the edges 37a, 37b are rounded, de-sharpened or ground smooth along all or part of their length so as to substantially eliminate or inhibit side cutting. Advantageously, rounded or de-sharpened edges limit the propensity for the edges 37a, 37b to catch on material within the osteotomy walls possibly creating vibration and/or undesirable enlarging of the hole during drilling or machining. If desired, one or more of the edges 37a, 37b may be sharpened so as to form side cutting edges.

In one embodiment, the leading edges 37a have a zero or neutral rake angle along substantially all or part of their length. In another embodiment, the leading edges 37a have a negative rake angle along substantially all or part of their length. In yet another embodiment, the leading edges 37a have a positive rake angle along substantially all or part of their length.

In the illustrated embodiments, the working portion 24 includes a generally longitudinal irrigation passage 40 (see FIG. 4) through the core 41. The passage 40 is in fluid communication with the collar through hole 32 (see FIG. 2) and hence the mounting shank passage 30 (see FIG. 3). The passage 40 is generally cylindrical in shape and is located substantially centrally within the working portion 24. The passage 40 is dimensioned and configured to accommodate insertion of an irrigation cannula, as discussed later herein, for washing away bone debris/chips (and tissue) and lubricating and cooling the drilling bit 10. In other embodiments, the irrigation passage 40 may be efficaciously dimensioned and configured in a modified manner, as required or desired, giving due consideration to the goals of providing efficient drilling performance, and/or of achieving one or more of the benefits and advantages as disclosed, taught or suggested herein.

In the illustrated embodiments, the passageway 40 stops short of extending completely through the distal end 38 of the drill bit 10. Instead, passageway 40 communicates through discharge ports 42 (see FIGS. 1–2 and 6–8) formed near the distal end 38 of the working portion 24. The internal fluid passageway 40, in combination with the irrigation passage 30 and discharge ports 42 enable cooling/lubrication fluid, such as water, to be circulated to the bone cutting portions of the drill bit 10, as discussed later herein, for washing away bone debris/chips (and tissue) and lubricating and cooling the drilling bit 10.

In the illustrated embodiments, the fluid discharge ports 42 are located distally on the trailing blade surfaces 34b of each blade 34, adjacent to the end cutting blades 36. Advantageously, such placement minimizes the tendency for generated bone chips to become lodged in the fluid discharge holes 42 and possibly hinder the application of cooling/lubricating fluid during drilling operations. In other embodiments, the discharge ports or openings 42 may be efficaciously placed in a modified manner, as required or desired, giving due consideration to the goals of providing efficient and/or accurate drilling performance, and/or of achieving one or more of the benefits and advantages as disclosed, taught or suggested herein.

In the illustrated embodiments of FIGS. 1–8, each blade 34 comprises and terminates distally in a respective one of the end cutting blades or flutes 36. The end cutting blades 36 generally form the cutting tip or head 35 having the distal-most end or terminus 38. As discussed below, the cutting tip 35 is generally characterized by a plurality of facets or angled surfaces.

In the illustrated embodiments, each cutting blade or spade 36 (see FIGS. 5–8) has a leading end cutting edge 36a and a trailing end edge 36b forming a surface or facet 122 therebetween and a leading surface or facet 124 and a trailing surface or facet 120. Each leading end cutting edge 36a is defined at the junction or intersection of corresponding leading surfaces 124 and relief surfaces 122. Preferably, each blade 36 and/or cutting edge 36a extends from substantially the distal-most point or end 38 to a substantially outer-most or major periphery, boundary or perimeter 84 (see FIG. 5) of the cutting tip 35 and/or working portion 24.

In the illustrated embodiments, and as best seen in FIG. 5, the cutting tip 35 further comprises surfaces or facets 126 created by grinding of the blades 36, described later. Each facet 126 is associated with one of the blades 36 and located near the distal end 38. In the illustrated embodiments, one or more of the surfaces 120, 122, 124, 126 are angled with respect to the longitudinal axis 11. Preferably, the surfaces 120, 122, 124, 126 converge to essentially a point at the distal-most end or terminus 38 on the drill bit longitudinal axis 11.

In the illustrated embodiments, each end blade 36 (see FIG. 7) comprises or is associated with a leading side end edge 46a and a trailing side end edge 46b. In one embodiment, one or more of the edges 46a, 46b are rounded, de-sharpened or ground smooth along all or part of their length so as to substantially eliminate or inhibit side cutting. Advantageously, rounded or de-sharpened edges limit the propensity for the edges 46a, 46b to catch on material within the osteotomy walls possibly creating vibration and/or undesirable enlarging of the hole during drilling or machining. If desired, one or more of the edges 46a, 46b may be sharpened so as to form side end cutting edges.

In one embodiment, the leading edges 46a have a zero or neutral rake angle along substantially all or part of their length. In another embodiment, the leading edges 46a have a negative rake angle along substantially all or part of their length. In yet another embodiment, the leading edges 46a have a positive rake angle along substantially all or part of their length.

In the illustrated embodiments, and as best seen in FIG. 5, the cutting blades 36 and cutting edges 36a are arranged generally symmetrically about the central core or web 41 and/or the distal terminus 38. In other embodiments, the blades 36 and/or edges 36a may be efficaciously arranged and/or configured in a modified manner, for example, asymmetrically, as required or desired, giving due consideration to the goals of providing efficient and/or accurate drilling performance, and/or of achieving one or more of the benefits and advantages as disclosed, taught or suggested herein.

Figure 7:
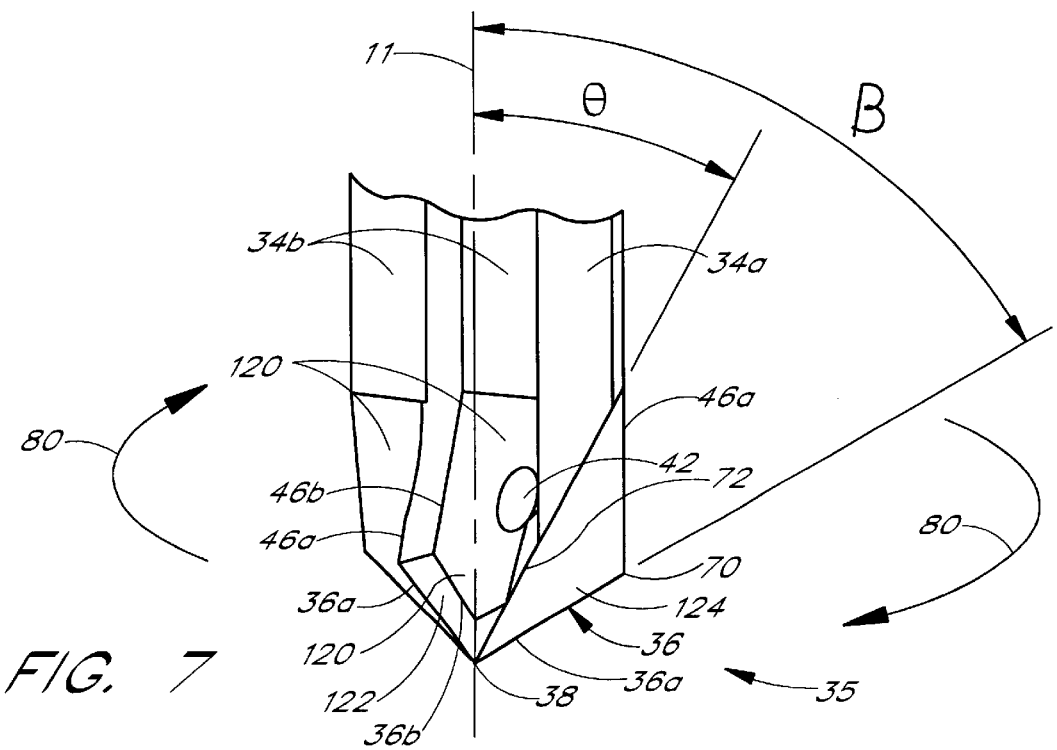
FIG. 7 is an enlarged view of the drill bit of FIG. 2 illustrating the cutting tip thereof.
Figure 6:
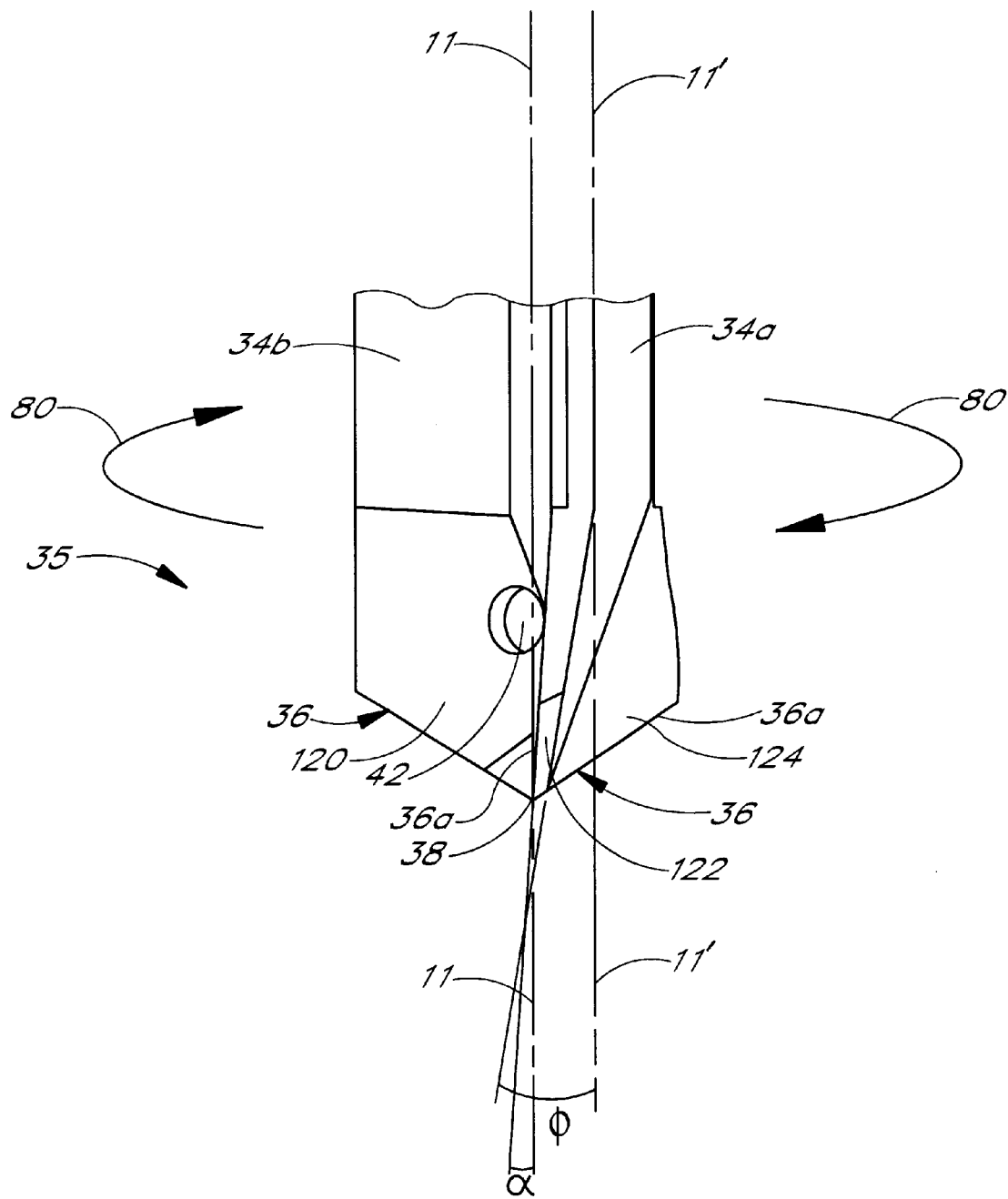
FIG. 6 is an enlarged view of the drill bit of FIG. 1 illustrating the cutting tip thereof.
Figure 8:
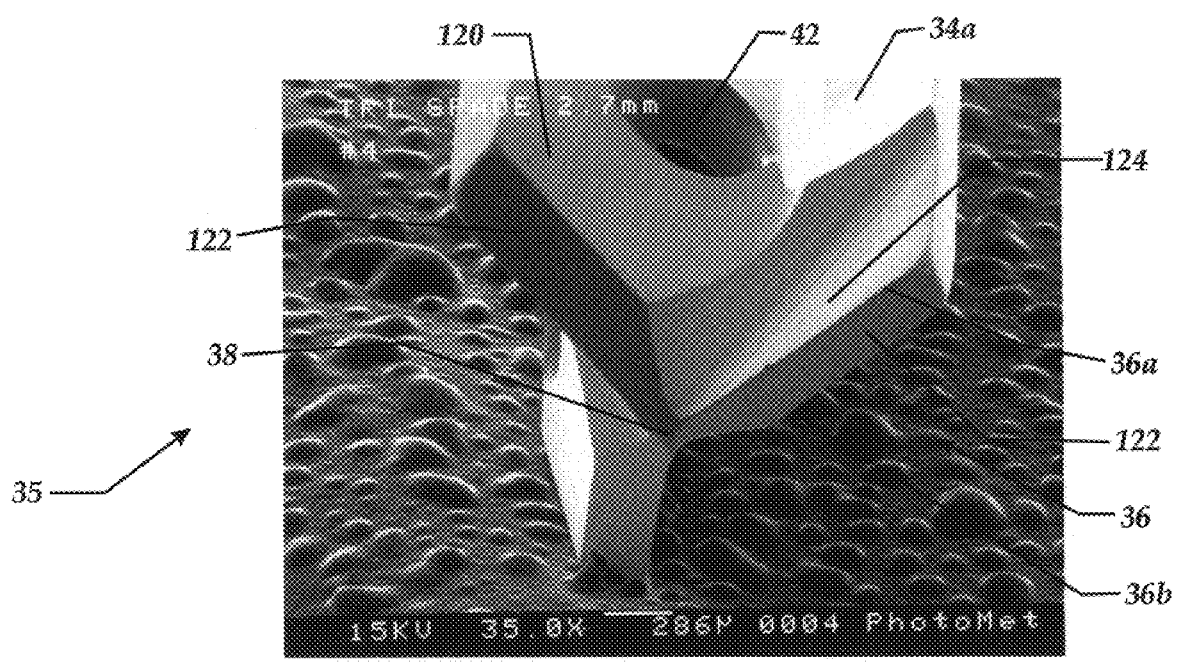
FIG. 8 is a 35× magnification microscopic photographic view of a dental drill bit illustrating the general geometry of the cutting tip thereof in accordance with one embodiment.

Preferably, and as best seen in FIGS. 6 and 7, the blades 36 extend substantially parallel to the shank longitudinal axis 11 along substantially most of the length of the cutting tip 35. In other embodiments, the one or more of the blades 36 may be efficaciously arranged and/or configured in a modified manner, as required or desired, giving due consideration to the goals of providing efficient and/or accurate drilling performance, and/or of achieving one or more of the benefits and advantages as disclosed, taught or suggested herein.

Preferably, and as shown in FIGS. 5–8, the cutting tip 35 includes three blades 36 and three cutting edges 36a. Advantageously, such a configuration provides for smooth and accurate drilling with substantially no wobbling. In another embodiment, the cutting tip 35 includes between three and six blades 36 and cutting edges 36a. In other embodiments, the cutting tip 35 may comprise more blades 36 and/or edges 36a with efficacy, as required or desired, giving due consideration to the goals of providing smooth and/or accurate drilling performance, and/or of achieving one or more of the benefits and advantages as disclosed, taught or suggested herein.

Preferably, and as best seen in FIG. 5, the cutting tip 35 includes three blades 36 approximately equally spaced 120° apart. In other embodiments, the cutting tip 35 may comprise more blades 36 spaced apart or offset in other angular configurations with efficacy, as required or desired, giving due consideration to the goals of providing efficient and/or accurate drilling performance, and/or of achieving one or more of the benefits and advantages as disclosed, taught or suggested herein.

Preferably, and as best seen in FIG. 5, the cutting tip 35 includes three end cutting edges 36a approximately equally spaced 120° apart. In other embodiments, the cutting tip 35 may comprise more end cutting edges 36a spaced apart or offset in other angular configurations with efficacy, as required or desired, giving due consideration to the goals of providing efficient and/or accurate drilling performance, and/or of achieving one or more of the benefits and advantages as disclosed, taught or suggested herein.

The leading surfaces 124 are preferably undercut surfaces formed in the leading surfaces 34a of respective blades 34. Preferably, the surfaces 124 are angled or slanted with respect to the longitudinal central rotary axis 11 or an axis generally parallel to the axis 11 to form a positive rake angle $\alpha$ (see FIG. 6) at respective leading edges 36a. Advantageously, the use of such a positive rake angle provides for efficient cutting and/or drilling when forming an osteotomy in a patient's jawbone.

Figure 9:
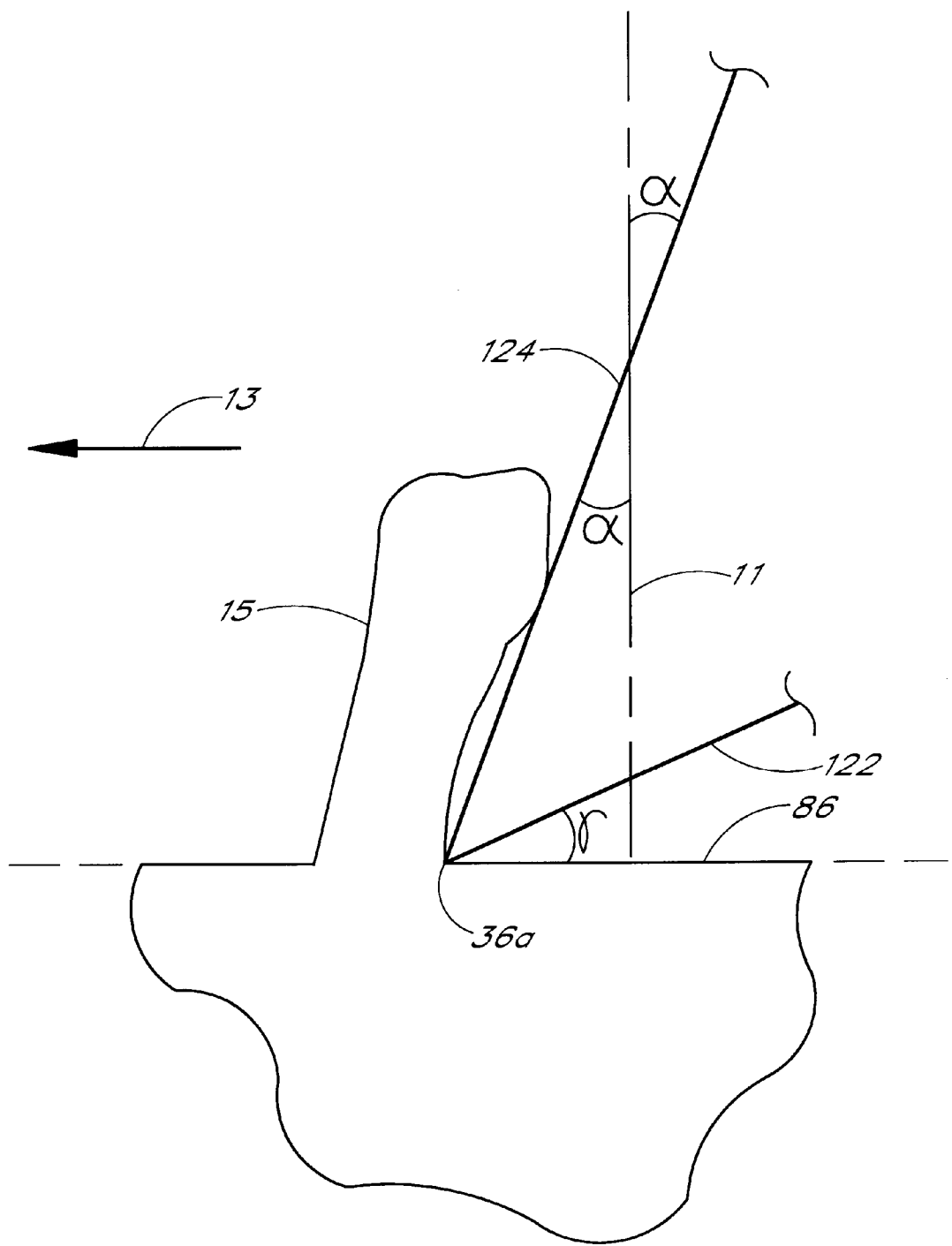
FIG. 9 is a schematic view of a drill bit cutting edge and face (not to scale) illustrating the general definition of a positive rake angle in accordance with one or more embodiments.

FIG. 9 is a simplified schematic two-dimensional illustration of a positive rake angle $\alpha$ as generally defined herein in accordance with one embodiment. In general, "rake" is a term of art and is typically defined as the angular relationship between a cutting face, or a tangent to the cutting face at a given point and a given reference plane or line. The rake angle is positive if the rake face 124 (the surface upon which a cut chip 15 slides as it leaves the cutting zone) is tilted away from (or leans backwards relative to) the direction of tool travel or rotation 13. Thus, the cutting edge 36a leads the surface of the cutting face 124 in rotation. Stated differently, a positive rake makes the inclination of the tool face 124 "keener or more acute" than when the rake angle is zero. In other words, the cutting edge 36a is rearwardly raked relative to the direction of tool travel or rotation 13 (to form positive rake surface 124) and hence be able to cut into a surface engaged by the rotating tool bit 10.

In one embodiment, the positive rake angle $\alpha$ (see FIG. 9) is generally defined by the angle between the rake face or surface 124 (or a plane containing the cutting face 124) and the longitudinal central rotary axis 11 of the bit 10 or an axis generally parallel to the axis 11. In another embodiment, the positive rake angle $\alpha$ is generally defined by the angle between the rake face or surface 124 (or a plane containing the cutting face 124) and an axis generally perpendicular to the surface being drilled into or machined.

In one embodiment, the positive rake angle $\alpha$ at one or more of the end cutting edges 36a is between about 4° and about 6°. In another embodiment, the positive rake angle $\alpha$ at one or more of the end cutting edges 36a is between about 2° and about 7°. In yet another embodiment, the positive rake angle $\alpha$ at one or more of the end cutting edges 36a is between about 1° and about 20°. However, those skilled in the art will readily recognize that the degree of raking can be tailored to optimize performance of the drill bit 10 according to the needs of the particular technique being performed and/or the preferences of the surgeon. In other embodiments, the positive rake angle at one or more of the end cutting edges 36a may efficaciously be less or more, as required or desired, giving due consideration to the goals of providing efficient and/or accurate drilling performance, and/or of achieving one or more of the benefits and advantages as disclosed, taught or suggested herein.

Preferably, all the cutting blades 36 comprise positive rake end cutting edges 36a. In another embodiment, at least one of the cutting blades 36 comprises a positive rake cutting edge 36a. In modified embodiments, one or more of the blades 36 may efficaciously comprise edges 36a raked in a modified manner along substantially all or part of their length, as required or desired, giving due consideration to the goals of providing efficient and/or accurate drilling performance, and/or of achieving one or more of the benefits and advantages as disclosed, taught or suggested herein.

In the illustrated embodiments, and as best seen in FIGS. 6 and 7, the positive rake cutting edges 36a extend or diverge, generally radially away from the longitudinal axis 11 at an acute (<90°) angle $\beta$, from substantially the central distal-most end or terminus 38 of the drill bit 10 to proximal ends 70 of the angled surfaces 122. Stated differently, the positive rake cutting edges 36a converge, generally radially towards the longitudinal axis 11 at an acute (<90°) angle $\beta$, from the proximal ends 70 to substantially the distal-most end or terminus 38 of the drill bit 10.

The ends 70 are generally at substantially the major or outermost diametric periphery of the working portion 24 and/or cutting tip 35. Thus, the diameter of the osteotomy formed is generally determined by this major diameter or circumferential size of the cutting tip 35. Having a positive rake preferably along substantially the entire length or span of the cutting edges 36a is particularly advantageous in enlarging a pre-existing hole or progressively enlarging an osteotomy by progressively using drill bits of different sizes, as is typically done.

In other embodiments, selected portions or sections of one or more of the cutting edges 36a may comprise a positive rake with efficacy, as required or desired, giving due consideration to the goals of providing efficient and/or accurate drilling performance, and/or of achieving one or more of the benefits and advantages as disclosed, taught or suggested herein. For example, positive rake cutting edges 36a may be provided on sections of one or more of the cutting edges 36a spaced from the distal end or point 38 or intermediate the distal point 38 and outer-most diameter of the cutting tip 35. Optionally, positive rake cutting edges 36a may be provided at sections of one or more of the cutting edges 36a adjacent to the distal end or point 38.

In one embodiment, the positive rake cutting edges 36a and positive rake surfaces 124 (see, for example, FIG. 7) sweep forward of leading blade surfaces 34a, as generally described and illustrated herein. The resulting "swept-forward" cutting edges are particularly advantageous and clinically efficacious for drilling osteotomies in human bone. Such swept-forward positive rake cutting edges also improve cutting efficiency and bone chip formation and removal. In accordance with one embodiment, "forward-swept" cutting edge shall be understood to mean any cutting edge that extends beyond a generally planar surface comprising a leading blade surface of a rotary drill bit.

In the illustrated embodiments, and as schematically shown in FIG. 9, the primary relief surfaces 122 form an edge relief angle $\gamma$ with respect to a plane 86 generally perpendicular to the longitudinal axis 11 or to the surface of the material being drilled into or machined. In one embodiment, the relief surfaces 122 are cut at an angle $\gamma$ with respect to a plane 86 generally perpendicular to the longitudinal axis 11 or to the surface of the material being drilled into or machined. The edge relief is provided between the leading edges 36a and respective trailing edges 36b. The cutting edge relief angle $\gamma$ controls the rate of penetration and the cutting efficiency of the drill 10. In one embodiment, the edge relief angle $\gamma$ is in the range from about 30° to about 35°. In other embodiments, the relief surfaces 122 may be efficaciously configured in a modified manner, as required or desired, giving due consideration to the goals of providing efficient and/or accurate drilling performance, and/or of achieving one or more of the benefits and advantages as disclosed, taught or suggested herein.

In the illustrated embodiments, and as shown in FIG. 7, the leading blade surfaces 124 have inner edges 72 oriented at an angle $\theta$ with respect to the longitudinal axis 11. In one embodiment, the leading blade surfaces 124 are formed by cutting at a compound angle $\theta$ with respect to the longitudinal axis 11. In one embodiment, the angle $\theta$ is in the range from about 20° to about 25°. In other embodiments, the blade surfaces 124 may be efficaciously configured in a modified manner, as required or desired, giving due consideration to the goals of providing efficient and/or accurate drilling performance, and/or of achieving one or more of the benefits and advantages as disclosed, taught or suggested herein.

In the illustrated embodiments, and as shown in FIG. 7, the drill point angle $\beta$ is about 60°. In other embodiments, the drill point angle may be efficaciously selected in a modified manner, as required or desired, giving due consideration to the goals of providing efficient and/or accurate drilling performance, and/or of achieving one or more of the benefits and advantages as disclosed, taught or suggested herein.

In the illustrated embodiments, and as shown in FIG. 6, the trailing blade surfaces 120 form an angle $\phi$ with respect to an axis 11' generally parallel to the longitudinal axis 11 or with respect to the longitudinal axis 11. In one embodiment, the trailing blade surfaces 120 are formed by cutting at an angle $\phi$ with respect to an axis 11' generally parallel to the longitudinal axis 11 or with respect to the longitudinal axis 11. The angle $\phi$ results in secondary relief surfaces on the trailing blade surfaces 120 for enhanced clearance. In one embodiment, the angle $\phi$ is in the range from about 8° to about 12°. In other embodiments, the surfaces 120 may be efficaciously configured in a modified manner, as required or desired, giving due consideration to the goals of providing efficient and/or accurate drilling performance, and/or of achieving one or more of the benefits and advantages as disclosed, taught or suggested herein.

Preferably, the central core or webbing 41 (see FIG. 4) of the drill bit 10 is made as small as reasonably possible at the distal-most end 38 (see, for example, FIGS. 6 and 7) of the cutting tip 35 and approximates a point at the distal-most tip 38. Minimal web diameter at the distal end 30 is advantageous in maximizing the cutting effectiveness of the cutting tip 35 and the end cutting edges 36a, reducing friction at the cutting tip 35, and improving chip formation and removal.

The web diameter throughout the remaining portion of the working portion 24 is less critical, but is preferably large enough to provide overall drill bit integrity, adequate irrigation, and resistance to collapse under torsion loads. On the other hand, the web diameter is not so large as to unduly reduce the size of the lateral channels 39. In one embodiment, the web diameter need not be constant along the length of the drill bit 10, but may be tapered, as desired, to provide, for example, a smaller web diameter toward the distal end 38 or any other similar variations desired.

In the illustrated embodiments, and as best seen in FIGS. 5–8, the fluid discharge ports 42 are located on the trailing blade surfaces 36b of each end cutting blade 36, adjacent to the end cutting edges 36b. Advantageously, such placement minimizes the tendency for generated bone chips to become lodged in the fluid discharge holes 42 and possibly hinder the application of cooling/lubricating fluid during drilling operations. In other embodiments, the discharge ports or openings 42 may be efficaciously placed in a modified manner, as required or desired, giving due consideration to the goals of providing efficient and/or accurate drilling performance, and/or of achieving one or more of the benefits and advantages as disclosed, taught or suggested herein.

In the illustrated embodiments, and as shown in FIGS. 1 and 2, the working portion 24 includes a plurality of depth indicating bands, indicia or markings 44 spaced from one another at predetermined intervals. The bands 44 provide a visual indicator of the depth of bone penetration and are, in one embodiment, distinguishable in surface relief and/or color from the remainder of the outer surface of the working portion 24. The bands 44 can be formed in grooves that fully or partially circumscribe the perimeter of the shank 25. The depth indicating bands 44 may be conveniently formed in a variety of shapes, sizes and colors by laser etching or by other processes, such as chemical etching, mechanical grinding/polishing, and the like.

In the illustrated embodiments, and as shown in FIGS. 1 and 2, the working portion 24 includes four depth indicating bands 44. In other embodiments, the working portion 24 may include fewer or more bands 44, as required or desired, giving due consideration to the goals of providing generally reliable depth indicating means, and/or of achieving one or more of the benefits and advantages as disclosed, taught or suggested herein.

Figure 10:
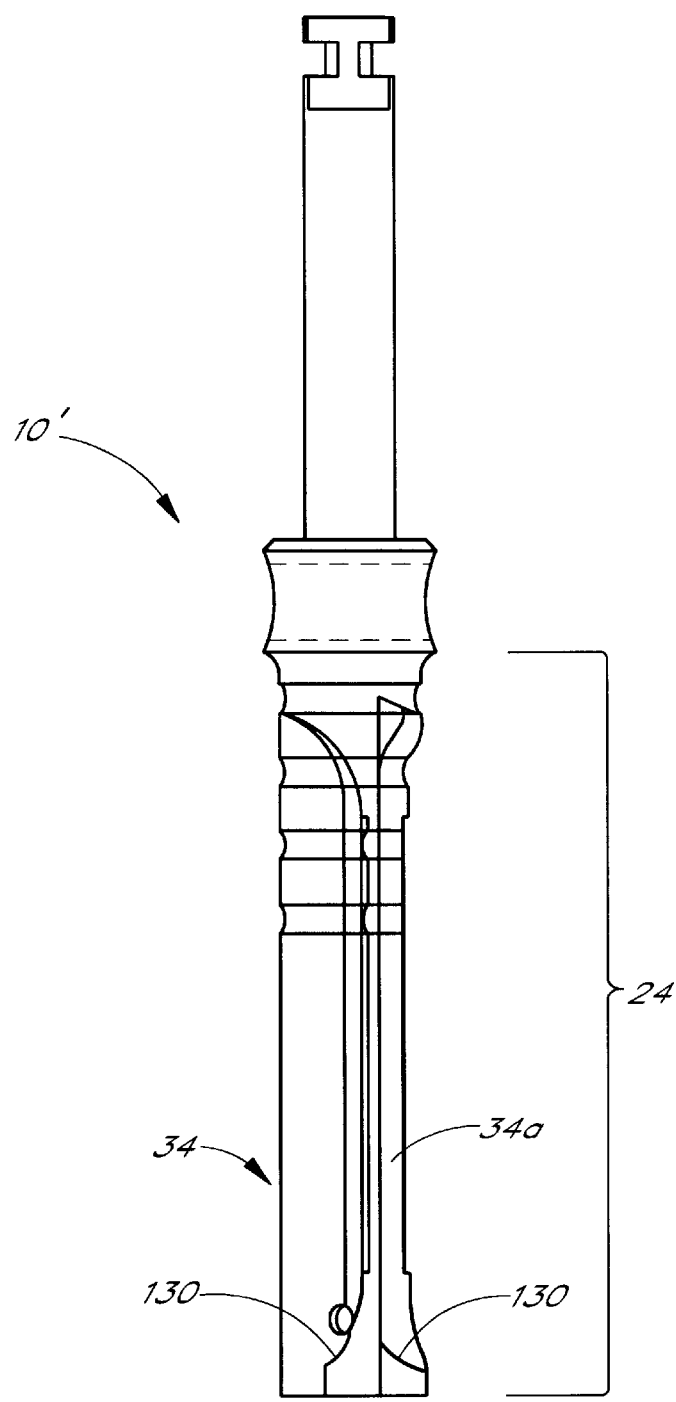
FIG. 10 is a side elevation view of a partially completed dental drill bit illustrating immediate machining prior to final grinding and/or machining of the cutting tip thereof in accordance with one embodiment.

To reliably form positive rake angle cutting edges 36a, preferably, the working portion 24 of the drill bit 10 is initially machined as illustrated by the partially completed drill bit 10' of FIG. 10. In one embodiment, the working portion 24 is machined so as to leave residual overhangs or lips 130 at or adjacent the distal ends of each blade 34 thereof. These lips 130 can advantageously be exploited by subsequent grinding and/or machining operations to provide end cutting blades 36 with positive rake end cutting edges 36a which sweep forward of leading blade surfaces 34a.

In one embodiment, and referring to FIG. 10, grinding and/or machining operations or sweeps are used to form the cutting tip 35 (see, for example, FIGS. 5–8) on the partially completed tool bit 10'. A series of grinding wheel sweeps or cuts is used to form the facets or angled surfaces 120, 122, 124, 126 on the cutting tip 35. The facets 126 are a consequence of a single grinding sweep being used to form each rake leading surface 124 and can be considered an extension of the leading surfaces 124. In one embodiment, the positive rake end cutting edges 36a are ground to a sharp edge.

In one embodiment, the drill bit 10 is fabricated from a rod of material by machining and/or grinding operations. In other embodiments, the drill bit 10 may be efficaciously manufactured by other techniques, as required or desired, such as casting, forging and/or molding, among other manufacturing techniques. The proximal mounting portion 22 and working portion 24 may be formed as a single integral structure or they may be formed separately and secured to one another at the collar 26 by welding, for example.

In one embodiment, the drill bit 10 is heat treated and electro-polished after final machining or forming is completed. In one embodiment, the drill bit 10 is also passivated after final machining or forming is completed.

In one embodiment, the drill bit 10 is fabricated from stainless steel. In another embodiment, the drill bit 10 is fabricated from UNS S45500 (ASTM-A564). In other embodiments, the drill bit 10 may be fabricated from a variety of other materials, such as metals, alloys, ceramics, plastics, as required or desired, giving due consideration to the goals of providing efficient and/or accurate drilling performance, and/or of achieving one or more of the benefits and advantages as disclosed, taught or suggested herein.

In one embodiment, the drill bit 10 has a length of about 38.1 mm (1.50 inches). In one embodiment, the mounting shank 22 has a length of about 14.5 mm (0.57 inches), the working portion 24 has a length of about 20.6 mm (0.81 inches), and the collar member 26 has a length of about 3.0 mm (0.12 inches). Of course, those skilled in the art will readily recognize that the drill bit 10 may be dimensioned and configured in a wide variety of other manners, as required or desired, depending on the particular nature of the osteotomy to be formed and the implant to be used.

In one embodiment, the working portion 24 is dimensioned and configured to provide a cutting or osteotomy diameter of about 3.8 mm (0.15 inches). In another embodiment, the working portion 24 is dimensioned and configured to provide a cutting or osteotomy diameter of about 2.7 mm (0.11 inches). In yet another embodiment, the working portion 24 is dimensioned and configured to provide a cutting or osteotomy diameter in the range from about 1.5 mm (0.06 inches) to about 6.0 mm (0.24 inches). In one embodiment, the working portion 24 is dimensioned to form an osteotomy having sufficient depth to house endosseous dental implants (not shown) with lengths ranging from about 8 mm (0.31 inches) to about 18 mm (0.71 inches). Of course, those skilled in the art will readily recognize that the drill bit 10 may be dimensioned and configured in a wide variety of other manners, as required or desired, depending on the particular nature of the osteotomy to be formed and the implant to be used.

The depth indicating bands 44 generally have a width within the range of from about 0.5 mm (0.02 inches) to about 1.5 mm (0.06 inches), and, in one embodiment about 0.76 mm (0.03 inches). In one embodiment, the bands 44 comprise grooves having a depth in the range from about 0.13 mm (0.005 inches) to about 0.25 mm (0.01 inches). The center-to-center spacing between adjacent bands 44 is in the range of from about 1 mm (0.04 inches) to about 4 mm (0.16 inches), and, in one embodiment, about 2.03 mm (0.08 inches). In one embodiment, the bands 44 comprise grooves having a depth in the range from about 0.13 mm (0.005 inches) to about 0.25 mm (0.01 inches). In other embodiments, the bands 44 may be dimensioned and configured in a wide variety of manners, as required or desired, giving due consideration to the goals of providing generally reliable depth indicating means, and/or of achieving one or more of the benefits and advantages as disclosed, taught or suggested herein.

Referring in particular to FIG. 5, in one embodiment, the major width W of the relief surfaces 122 is about 0.30 mm (0.012 inches). In other embodiments, the relief surfaces 122 may be dimensioned in a modified manner with efficacy, as required or desired, giving due consideration to the goals of providing efficient and/or accurate drilling performance, and/or of achieving one or more of the benefits and advantages as disclosed, taught or suggested herein.

Surface Coatings

In one embodiment, at least a portion or selected surfaces of the tool bit or dental instrument 10 is coated with an amorphous hard carbon coating or film 20, as schematically illustrated in FIG. 11. The coating 20 can comprise, for example, a diamond-like carbon (DLC) coating 20, an amorphous diamond coating 20, a crystalline diamond coating 20, or a combination thereof. The coating 20 can be multi-layered and comprise one or more layers. The term "hard carbon," as used herein, can denote any or all of the above. Some embodiments of diamond-like carbon coated dental instruments are disclosed in U.S. patent application Ser. No. 09/439,247, filed Nov. 12, 1999 and U.S. patent application Ser. No. 09/853,256, filed May 11, 2001, the entire disclosure of each one of which is hereby incorporated by reference herein.

In one embodiment, the coating 20 is a diamond-like carbon (DLC) coating 20. In another embodiment the coating 20 comprises an amorphous diamond coating 20. Generally, diamond-like carbon (DLC) is hydrogenated and this feature distinguishes it from amorphous diamond which has a smaller or negligible proportion of hydrogen. Both comprise an amorphous arrangement of atoms and a major or substantially sizable proportion of $sp^3$ bonding which results in high mechanical hardness, low friction, chemical inertness (biocompatibility), more heat transfer, and other desirable properties. Diamond-like carbon (DLC) and amorphous diamond can also include some degree of $sp^2$ bonding. In general, the amorphous "hard carbon" coating 20 as disclosed herein comprises (a) at least some $sp^3$ bonding, (b)

some, negligible or no sp² bonding, and (c) some, negligible or no hydrogenation. A discussion of sp$^n$ bonding configurations is available in many references, for example, "Synthetic Diamond: Emerging CVD Science and Technology," edited by K. E. Spear and J. P. Dismukes (sponsored by the Electrochemical Society, Inc.), Wiley, N.Y., 1994.

One advantage of the coating 20 is that it provides a reduced coefficient of friction (enhanced lubriciousness) between the jawbone and the rotating coated dental tool bit 10. Some of the other benefits and advantages arise as a consequence of the coating 20 properties of high mechanical hardness (wear resistance), corrosion resistance, high thermal conductivity and biocompatibility.

Preferably, substantially the entire or most of the working portion 24 is coated with a diamond-like carbon (DLC) or amorphous diamond film 20. In another embodiment, the cutting tip 35 only is coated with a diamond-like carbon (DLC) or amorphous diamond film 20. It is generally preferred that the proximal mounting portion 22 not be coated to maintain good frictional contact and to avoid the possible creation of unwanted carbon particulate matter when the bit is frictionally engaged with a hand-piece or drill. In modified embodiments, some or all of the mounting shank 22 may be coated with diamond-like carbon (DLC) or amorphous diamond, as required or desired. For example, the chuck 28 of the mounting shank 22 may be coated with diamond-like carbon (DLC) or amorphous diamond to advantageously facilitate easy insertion/removal of the bit 10 into/from a hand-piece or drill.

Preferably, the collar 26 is also coated with diamond-like carbon (DLC) or amorphous diamond. The coating can reduce adhesion of any bone chips or other debris to the collar member 26, and thus make it easier to clean and sterilize the drill bit 10. The coating also desirably improves the corrosion resistance of the collar member 26.

In general, an amorphous "hard carbon" coating or film 20 may be applied to selected surfaces of the tool bit 10 in a wide variety of configurations, as required or desired, giving due consideration to the goal of improving performance. In one embodiment, the coating 20 is formed by a physical vapor deposition (PVD) and/or chemical vapor deposition (CVD) technique, though other coating techniques may be efficaciously utilized, as required or desired.

In one embodiment, the hard carbon coating 20 has a thickness of about 1 micron ($\mu$m). In another embodiment, the hard carbon coating 20 has a thickness in the range from about 0.5 microns ($\mu$m) to about 2.0 microns ($\mu$m). In yet another embodiment, the hard carbon coating 20 has a thickness in the range from about 0.5 microns ($\mu$m) to about 100 microns ($\mu$m). In other embodiments, the thickness of the hard carbon coating 20 may be selected, as required or desired, giving due consideration to the goal of achieving one or more of the benefits and advantages as disclosed, taught or suggested herein.

In one embodiment, the hard carbon coating 20 comprises between about 70% to about 100% sp³ bonding. In other embodiments, the coating 20 can comprise less sp³ bonding, as required or desired, giving due consideration to the goal achieving one or more of the benefits and advantages as disclosed, taught or suggested herein.

In one embodiment, the hydrogen content of the hard carbon is between about 5 to about 35 atomic %. In other embodiments, the hydrogen content can be less or more, as required or desired, giving due consideration to the goal achieving one or more of the benefits and advantages as disclosed, taught or suggested herein.

In one embodiment, the hard carbon coating 20 has a coefficient of friction of about 0.1. In another embodiment, the hard carbon coating 20 has a coefficient of friction in the range from about 0.01 to about 0.1. In other embodiments, the hard carbon coating can have a lower or higher coefficient of friction, as required or desired, giving due consideration to the goal of achieving one or more of the benefits and advantages as disclosed, taught or suggested herein.

In one embodiment, the hard carbon coating 20 has a Knoop hardness of about 2000 kg/mm². In other embodiments, the hard carbon coating 20 can have a lower or higher hardness, as needed or desired, giving due consideration to the goal of achieving one or more of the benefits and advantages as disclosed, taught or suggested herein.

The hard carbon coating 20 can comprise a wide variety of commercially available "hard carbon" coatings including, but not being limited to, diamond-like carbon (DLC), amorphous diamond, crystalline diamond, or a combination thereof. For example, if the inclusion of a certain proportion of crystalline structure is advantageous for a particular dental application, the coating 20 may include a certain quantity of crystalline diamond along with diamond-like carbon (DLC) and/or amorphous diamond. Also, the coating 20 may be doped with small quantities of other materials to achieve a desired synergistic balance of the desirable properties of hard carbon coatings.

Suitable hard carbon coatings can be formed by a variety of techniques, for example, physical vapor deposition (PVD) processes and chemical vapor deposition (CVD) processes. The physical vapor deposition (PVD) may comprise single-ion beam sputtering, dual ion-beam sputtering, and radio-frequency (RF) sputtering, among others. The chemical vapor deposition (CVD) may include hot-filament CVD, plasma-assisted CVD (PACVD), direct-current (DC) PACVD, radio-frequency (RF) PACVD, direct-current (DC) thermal plasma (CVD), radio-frequency (RF) thermal plasma CVD, and flame CVD, among others.

It is desirable to clean the substrate surface prior to applying the coating. This facilitates better adherence of the hard carbon coating 20 to the drill bit 10. In one embodiment, this cleaning process utilizes ultrasonic cleaning followed by a plasma cleaning of the tool bit 10. The plasma cleaning step includes bombardment of the tool bit 10 by suitable ions, such as argon ions. In one embodiment, a combination of physical vapor deposition (PVD) and chemical vapor deposition (CVD) techniques is used to form the hard carbon coating 20 on the tool bit 10. The cleaning process and application of the coating can be performed by any one of a number of commercial coating providers. Of course, a variety of other suitable coatings and techniques may be utilized with efficacy, as required or desired, giving due consideration to the goals of providing a hard coated, corrosion resistant dental cutting tool, and/or of achieving one or more of the benefits and advantages as disclosed, taught or suggested herein.

In one embodiment, one or more osteotomy depth indicating bands, indicia or markings are provided on the coated tool bit 10 by a laser etching or pseudo-etching surface treatment. The bands are colored or shaded distinctly or in contrast to the adjacent surface(s) of the tool bit 10 to provide visual differentiation. For example, generally white or light gray bands on a generally black or dark gray hard carbon tool bit 10. Advantageously, the surface processing of the coated tool bit 10 to form the bands does not adversely affect one or more of the desirable bulk properties, for example, the corrosion resistance, of the coating 20. Some embodiments of pseudo-etching of diamond-like carbon coated dental instruments are disclosed in U.S. patent application Ser. No. 09/853,256, filed May 11, 2001, the entire disclosure of which is hereby incorporated by reference herein.

In one embodiment, at least a portion or selected surfaces of the tool bit or dental instrument 10 is coated with a titanium nitride coating or film 20', as schematically illustrated in FIG. 11. Titanium nitride provides a hard, corrosion-resistant and biocompatible coating on the tool bit 10.

Preferably, substantially the entire or most of the working portion 24 is coated with a titanium nitride film 20'. In another embodiment, the cutting tip 35 only is coated with a titanium nitride film 20'. In a further embodiment, the collar 26 is also coated with a titanium nitride film 20'. Optionally, the mounting shank 22 may be coated with titanium nitride, as needed or desired.

Operation

In accordance with one embodiment, FIG. 12 illustrates the use of a dental drilling/cutting system or apparatus 110 to form an osteotomy in a bone material 76 of a patient's jawbone. The drilling system 110 generally includes the tool or drill bit 10 connected to a drill or handpiece 12 for providing rotor torque to the tool bit 10. The handpiece 12 may be powered by a wide variety of commercially available power sources, such as pneumatic, hydraulic or electric motors, as is known in the art.

Preferably, the drilling system 110 further includes an irrigation cannula 14 (see FIG. 12). The irrigation cannula 14 is supported by a support member 16 on the handpiece 12. The irrigation cannula 14 is in fluid communication with the tool bit 10 and provides fluid, for washing and cooling, during operation.

In use, the motorized handpiece 12 (see FIG. 12) is held in the operator's hand and the drill bit 10 is positioned at the desired osteotomy site. The handpiece 12 provides rotational motion to the drill bit 10 for cuttingly and/or chiselingly penetrating the patient's jawbone 76. The procedure can involve the use of one or more sizes or types of tool bits. Typically, the procedure involves using drill bits 10 of progressively increasing size to gradually increase the size of the osteotomy. In the latter stages, the size of the drill bit 10 in conjunction with the depth indicating bands 44 are utilized to finalize the size and depth of the osteotomy as predetermined or dictated by a particular implant selected by the oral surgeon. One or more osteotomies may be prepared in this manner, as dictated by the particular needs of the patient.

During drilling operations, the irrigation cannula 14 extends through the mounting shank passage 30, a plug or seal 78 (see FIG. 12) in the collar 32 and into the internal fluid passageway 40 of the working portion 24, thereby rendering the irrigation cannula 14 in fluid communication with the osteotomy being formed. The plug 78 serves to hold the irrigation cannula 14 in place and prevent undesired back-flow of cooling fluid through the irrigation passage 30.

The internal fluid passageway 40, in combination with the irrigation passage 30 and discharge ports 42 enable cooling/lubrication fluid, such as water, to be circulated to the bone cutting portions of the drill bit 10. The irrigation fluid serves to cool and lubricate the area being drilled or machined, including intermediate points along the working portion 24 of the shank 25. Additionally, the fluid aids in the removal of bone chips and other debris from the work surface via the channels 39. Typically, a saline solution or sterile water is used as the irrigation fluid.

During drilling, bone chips are generated by the end cutting edges 36a. These are initially driven forward by the leading blade surfaces 124 and/or the leading blade surfaces 34a as the drill bit 10 rotates clockwise, generally indicated by arrows 80 (see FIG. 12). The forward-swept positive rake angle leading end cutting edges 36a facilitate lifting and removal of the chips and other debris from the immediate cutting area, increasing the efficiency of the cutting operation.

The primary relief surfaces 122 and/or the small web size at the distal end 38 also increase the efficiency of the cut, by minimizing the amount of surface area of bone in contact with the drill bit 10 in the vicinity of the end cutting edges 36a. The trailing secondary relief surfaces 120 and/or the small web size at the distal end 38 provide enhanced bone chip and debris clearance. Bone chips and debris 140 are continuously flushed out of the osteotomy by cooling solution flowing down through cannula 14, down through the drill shank 25, out through discharge ports 42 of drill bit 10 and up through the channels 39, as generally indicated by arrows 150 (see FIG. 12).

The positive rake angle on the leading end cutting edges 36a provides for efficient, accurate and safe osteotomy forming operations. The cutting of bone material by the positive rake angle edges 36a reduces the torque and/or force needed for drilling. On the other hand, it advantageously increases the speed of the operation. Desirably, this translates into less discomfort, if any, for the patient. Additionally, the reduced drilling torque and/or force decrease the chances of bone or tissue damage or "necrosis" by frictional overheating.

Figure 13:
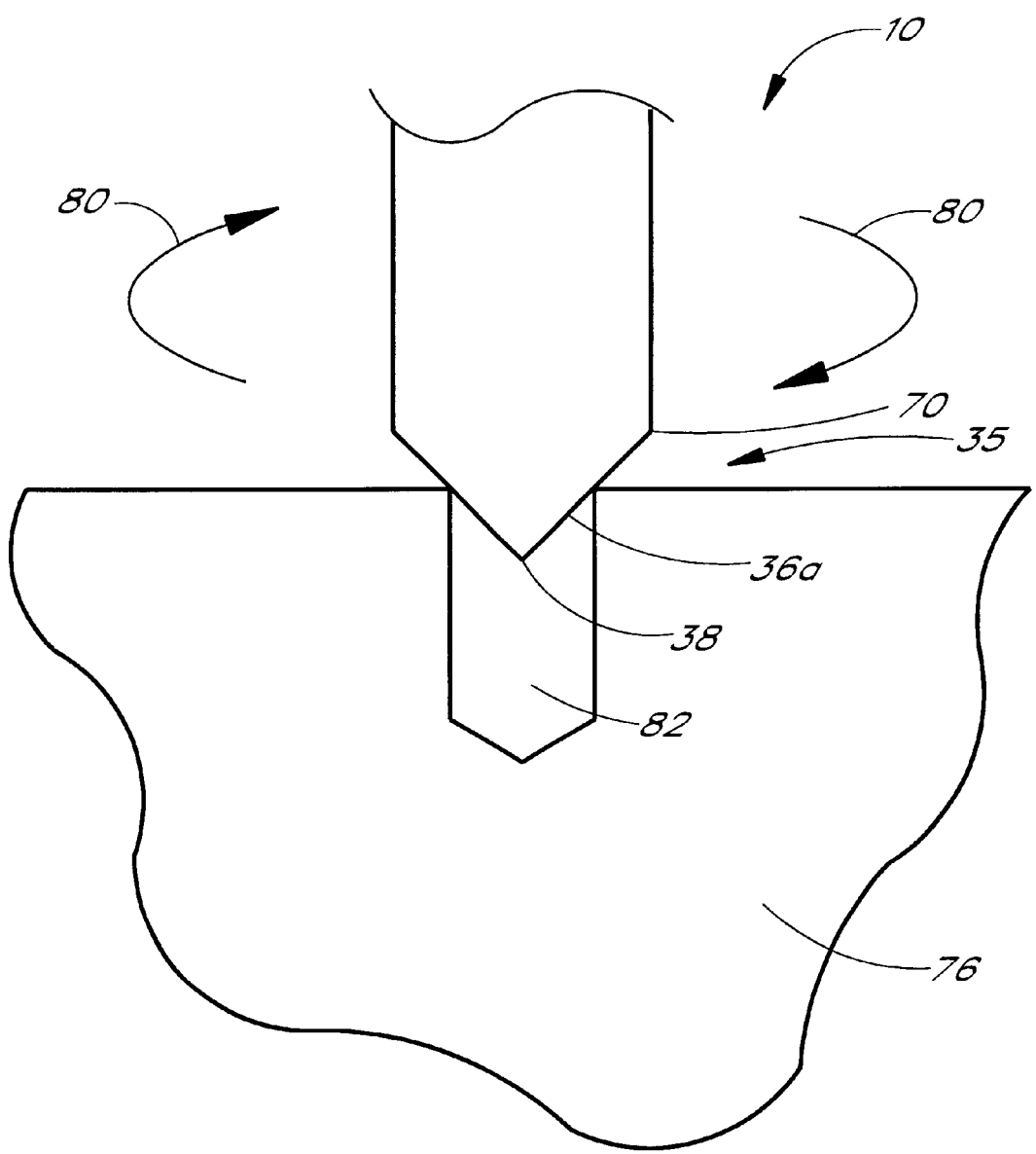
FIG. 13 is a schematic view illustrating enlargement of a pre-existing osteotomy by a dental drill bit having a positive rake angle on substantially the entire length of a cutting edge thereof in accordance with one embodiment.

It is advantageous that, preferably, the positive rake angle is provided along substantially the entire length or working/cutting span of one or more of the leading end cutting edges 36a. This allows for efficient cutting along the entire length of the leading end cutting edge 36a. Thus, the drill bit 10 or cutting tip 35 will efficiently cut bone when preparing a fresh osteotomy or when enlarging an already formed or pre-existing osteotomy or jawbone cavity 82 (see FIG. 13). Typically, drill bits of different sizes are used to progressively enlarge an osteotomy to the desired size.

While the components and techniques of the invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A drill bit for preparing surgical sites for placement of endosseous dental implants, comprising:

a mounting shank having a chuck at a proximal end sized and configured to interface with a rotation providing hand-piece;

a distal cutting head comprising a plurality of end blades each having an end cutting edge with a positive rake angle converging radially from substantially an outer-most diameter of said cutting head to substantially a distal-most point of said cutting head; and a plurality of side blades intermediate said mounting shank and said distal cutting head, each of said side blades being substantially straight and extending radially to a distance about the same as said outer-most diameter, each of said side blades having a side edge which terminates proximate to said outer-most diameter, each of said side edges being substantially rounded so as to substantially eliminate or inhibit side cutting.

2. The drill bit of claim 1, wherein said drill bit has a longitudinal axis and said side are arranged substantially parallel to said longitudinal axis.

3. The drill bit of claim 1, wherein said drill bit has a longitudinal axis and said side extend substantially straight generally along said longitudinal axis.

4. The drill bit of claim 1, wherein said drill bit has a longitudinal axis and said side are angularly spaced apart about said longitudinal axis.

5. The drill bit of claim 1, wherein each of said end blades comprises one or more relief surfaces.

6. The drill bit of claim 1, wherein said positive rake angle is in the range from about 4° to about 6°.

7. The drill bit of claim 1, wherein said positive rake angle is in the range from about 2° to about 7°.

8. The drill bit of claim 1, wherein said positive rake angle is in the range from about 1° to about 20°.

9. The drill bit of claim 1, wherein said cutting head is coated with diamond-like carbon.

10. The drill bit of claim 1, wherein said cutting head is coated with amorphous diamond.

11. The drill bit of claim 1, wherein said cutting head is coated with titanium nitride.

12. The drill bit of claim 1, wherein said cutting head is sized to prepare an osteotomy having a diameter in the range from about 1.5 mm to about 6 mm.

13. The drill bit of claim 1, wherein said cutting head comprises at least three of said end blades.

14. The drill bit of claim 1, wherein each of said end blades has a leading surface distally terminating in one of said cutting edges and each of said leading surfaces is tilted away from the direction of drill bit rotation to provide said positive rake angle.

15. A dental tool bit for forming an endosseous implant-receiving osteotomy in bone material, comprising:
a shank having a rotary longitudinal axis, said shank comprising:
a mounting portion adapted to interface with a dental hand-piece; and
a working portion having a distal terminus and an outer-most perimeter, said working portion comprising a plurality of blades extending generally parallel to said longitudinal axis, each of said blades distally terminating in an end cutting blade, each of said end cutting blades having a leading surface with a leading end cutting edge, a trailing surface with a trailing end edge and a relief surface between said leading end cutting edge and said trailing end edge, each of said leading surfaces being ground to form an extending facet around said distal terminus, said facets being substantially symmetrically arranged around said distal terminus, said leading surfaces, said relief surfaces and said facets converging to substantially a point at said distal terminus, at least one of said end cutting blades having a positive rake angle, at least one of said end cutting blades having said positive rake angle along substantially its entire span extending radially from substantially said distal terminus of said working portion to substantially said outer-most perimeter of said working portion.

16. The tool bit of claim 15, wherein said positive rake angle is in the range from about 4° to about 6°.

17. The tool bit of claim 15, wherein said positive rake angle is in the range from about 2° to about 7°.

18. The tool bit of claim 15, wherein said positive rake angle is in the range from about 1° to about 20°.

19. The tool bit of claim 15, wherein said mounting portion and said working portion are connected by a collar member.

20. The tool bit of claim 15, wherein said tool bit comprises a longitudinal passage in fluid communication with a plurality of discharge ports.

21. The tool bit of claim 15, wherein said discharge ports are located on said trailing surfaces.

22. The tool bit of claim 15, wherein said working portion comprises a plurality of depth indicating indicia.

23. The tool bit of claim 15, wherein each of said blades comprises substantially rounded side edges.

24. The tool bit of claim 15, wherein said working portion is coated with a material selected from the group consisting of: diamond-like carbon, amorphous diamond and titanium nitride.

25. The tool bit of claim 15, wherein said working portion comprises at least three of said blades.

26. The tool bit of claim 15, wherein said leading surfaces are angled with respect to said longitudinal axis.

27. A dental drilling system for preparing an osteotomy, comprising:
a tool bit having a mounting shank, a cutting tip, a collar portion therebetween and a longitudinal irrigation passage, said cutting tip comprising a plurality of blades each distally terminating in an end cutting edge, each end cutting edge having a positive rake angle spanning substantially its entire length, at least one of said end cutting edges diverging from substantially a distal terminus of said cutting tip to substantially an outer-most periphery of said cutting tip, said collar portion comprising a transverse through hole in fluid communication with said irrigation passage and extending in a direction generally perpendicular to said irrigation passage; and
a dental hand-piece holding said tool bit and adapted to provide rotational motion to said tool bit.

28. The drilling system of claim 27, further comprising an irrigation cannula in fluid communication with said irrigation passage.

29. The drilling system of claim 27, wherein said tool bit has a longitudinal axis and said blades are arranged substantially parallel to said longitudinal axis.

30. The drilling system of claim 27, wherein said tool bit has a longitudinal axis and said blades extend substantially axially about said longitudinal axis.

31. The drilling system of claim 27, wherein said tool bit has a longitudinal axis and said blades are angularly spaced apart about longitudinal axis.

32. The drilling system of claim 27, wherein said positive rake angle is in the range from about 4° to about 6°.

33. The drilling system of claim 27, wherein said positive rake angle is in the range from about 2° to about 7°.

34. The drilling system of claim 27, wherein said positive rake angle is in the range from about 1° to about 20°.

35. The drilling system of claim 27, wherein said tool bit comprises a plurality of osteotomy depth indicating markings.

36. The drilling system of claim 27, wherein selected surfaces of said tool bit are coated with a material selected from the group consisting of: diamond-like carbon, amorphous diamond and titanium nitride.

37. The drilling system of claim 27, wherein said tool bit is sized to prepare an osteotomy having a diameter in the range from about 1.5 mm to about 6 mm.

38. The drilling system of claim 27, wherein said tool bit is sized to prepare an osteotomy having a depth sufficient to receive dental implants with lengths ranging from about 8 mm to about 18 mm.

39. The drilling system bit of claim 27, wherein said cutting tip comprises at least three of said blades.

40. The drilling system of claim 27, wherein each of said blades has a leading face terminating in one of said cutting edges and each of said leading faces leans backwards relative to the direction of drill bit rotation.

41. A dental tool bit for forming an implant-receiving osteotomy in a jawbone, comprising:

a shank having a substantially central longitudinal axis and a direction of rotation, said shank comprising:

a mounting portion having a chuck at a proximal end adapted to interface with a rotary dental hand-piece;

a working portion having a distal-most point and an outer-most perimeter, said working portion comprising a plurality of blades extending substantially parallel to said longitudinal axis, each of said blades having a leading surface distally terminating in an end cutting edge, each end cutting edge extending radially from substantially said distal-most point of said working portion to substantially said outer-most perimeter of said working portion, at least one of said leading surfaces being angled relative to said longitudinal axis such that it is tilted away from said direction of rotation; and a low friction coating on said working portion, said coating comprising amorphous diamond.

42. The tool bit of claim 41, wherein at least one of said leading surfaces comprises a positive rake face.

43. The tool bit of claim 41, wherein at least one of said end cutting edges has a positive rake angle.

44. The tool bit of claim 41, wherein said amorphous diamond comprises between about 70% to about 100% $sp^3$ bonding.

45. The tool bit of claim 41, wherein said amorphous diamond is hydrogenated.

46. The tool bit of claim 45, wherein said amorphous diamond comprises between about 5 to about 35 atomic % of hydrogen.

47. The tool bit of claim 41, wherein said working portion comprises a plurality of spaced depth indicating indicia formed a surface treatment of said coating.

48. The tool bit of claim 47, wherein said bands are white or light gray and said coating is dark gray or black, thereby providing visual differentiation.

49. A method of forming an osteotomy in bone material for receiving a dental implant by using a drill bit having a cutting tip comprising a plurality of end blades each having an end cutting edge with a positive rake angle converging radially from substantially an outer-most diameter of said cutting tip to substantially a distal-most point of said cutting tip, said method comprising the steps of:

positioning said drill bit at a selected osteotomy site;

engaging said drill bit with said bone material;

providing rotational motion to said drill bit to cut said bone material due to rotational interaction between said end cutting edges having said positive rake angle and said bone material to form said osteotomy; and limiting side cutting as said drill bit penetrates into said bone material by providing a plurality of side blades above said cutting tip, each of said side blades being substantially straight and extending radially to a distance about the same as said outer-most diameter, each of said side blades having a side edge which terminates proximate to said outer-most diameter, each of said side edges being substantially rounded so as to substantially eliminate or inhibit side cutting due to engagement of said side edges with said bone material.

50. The method of claim 49, comprising the further step of withdrawing said drill bit from said osteotomy when an osteotomy of a selected size has been formed.

51. The method of claim 49, comprising the further step of providing irrigation fluid to said drill bit to cool, lubricate and wash said drill bit and/or said osteotomy.

52. The method of claim 49, wherein said cutting tip comprises at least three of said blades.

53. The method of claim 49, wherein each of said end blades has a leading surface distally terminating in one of said cutting edges and each of said leading faces is tilted rearwardly relative to the direction of drill bit rotation to form said positive rake angle.

54. The method of claim 49, wherein said drill bit has a longitudinal axis and said blades are arranged substantially parallel to said longitudinal axis.

55. The method of claim 49, wherein said drill bit has a longitudinal axis and said blades extend substantially straight generally along said longitudinal axis.

* * * * *

UNITED STATES PATENT AND TRADEMARK OFFICE
CERTIFICATE OF CORRECTION

| | | |
|---|---|---|
| PATENT NO. | : 6,641,395 B2 | Page 1 of 1 |
| APPLICATION NO. | : 09/920351 | |
| DATED | : November 4, 2003 | |
| INVENTOR(S) | : Kumar et al. | |

It is certified that error appears in the above-identified patent and that said Letters Patent is hereby corrected as shown below:

At Title page, Item [56], column 2, line 8, after "5,868,572 A 2/1999 Lazzara et al. ....." delete "433/165" and insert --433/173--, therefor.

At column 5, line 53, delete "semicircular" and insert --semi-circular--, therefor.

At column 19, line 2, in Claim 2, after "side" insert --blades--.

At column 19, line 5, in Claim 3, after "side" insert --blades--.

At column 19, line 8, in Claim 4, after "side" insert --blades--.

At column 20, line 4, in Claim 21, delete "claim 15," and insert --claim 20,--, therefor.

At column 20, line 45, in Claim 31, after "about" insert --said--.

At column 21, line 39, in Claim 47, after "formed" insert --by--.

Signed and Sealed this

Twenty-second Day of May, 2007

JON W. DUDAS
*Director of the United States Patent and Trademark Office*